(12) United States Patent
Laske et al.

(10) Patent No.: US 7,103,418 B2
(45) Date of Patent: Sep. 5, 2006

(54) ACTIVE FLUID DELIVERY CATHETER

(75) Inventors: Timothy G. Laske, Shoreview, MN (US); Daniel C. Sigg, St. Paul, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 345 days.

(21) Appl. No.: 10/262,046

(22) Filed: Oct. 2, 2002

(65) Prior Publication Data

US 2004/0068299 A1  Apr. 8, 2004

(51) Int. Cl.
*A61N 1/05* (2006.01)
*A61M 31/00* (2006.01)

(52) U.S. Cl. ............... 607/120; 607/126; 607/127; 604/506; 604/175; 604/272

(58) Field of Classification Search ........... 607/116, 607/119, 120, 122, 126–128; 604/506, 175, 604/272
See application file for complete search history.

(56) References Cited

U.S. PATENT DOCUMENTS

| | | | |
|---|---|---|---|
| 3,737,539 A | 6/1973 | Jaeggi et al. | 424/248 |
| 4,106,512 A | 8/1978 | Bisping | 128/418 |
| 4,360,031 A | 11/1982 | White | 128/786 |
| 4,506,680 A | 3/1985 | Stokes | 128/786 |
| 4,606,118 A | 8/1986 | Cannon et al. | 29/825 |
| 4,774,951 A | 10/1988 | Osypka | |
| 5,002,067 A | 3/1991 | Berthelsen et al. | 128/786 |
| 5,143,090 A | 9/1992 | Dutcher et al. | 128/785 |
| 5,246,014 A | 9/1993 | Williams et al. | 607/122 |
| 5,353,800 A | 10/1994 | Pohndorf et al. | 128/673 |
| 5,396,902 A | 3/1995 | Brennen et al. | 128/772 |
| 5,431,649 A | 7/1995 | Mulier et al. | 606/41 |
| 5,447,533 A | 9/1995 | Vachon et al. | 607/120 |
| 5,496,360 A | 3/1996 | Hoffmann et al. | 607/120 |
| 5,507,743 A * | 4/1996 | Edwards et al. | 606/41 |
| 5,807,249 A | 9/1998 | Qin et al. | 600/374 |
| 5,827,216 A * | 10/1998 | Igo et al. | 604/21 |
| 5,837,006 A | 11/1998 | Ocel et al. | 607/127 |
| 5,851,506 A | 12/1998 | Zheng et al. | 423/592 |
| 5,906,613 A | 5/1999 | Mulier et al. | 606/41 |
| 5,987,746 A | 11/1999 | Williams | 29/876 |
| 6,010,526 A | 1/2000 | Sandstrom et al. | 607/1 |
| 6,052,625 A | 4/2000 | Marshall | 607/122 |
| 6,102,887 A | 8/2000 | Altman | 604/22 |
| 6,192,280 B1 | 2/2001 | Sommer et al. | 607/122 |
| 6,346,099 B1 | 2/2002 | Altman | 604/428 |
| 6,358,247 B1 * | 3/2002 | Altman et al. | 606/41 |
| 6,366,819 B1 | 4/2002 | Stokes | 607/119 |

(Continued)

FOREIGN PATENT DOCUMENTS

WO    WO 98/02040    1/1998

OTHER PUBLICATIONS

Guerrero et al., "Slow Ventricular Conduction in Mice Heterozygous for a Connexin43 Null Mutation", *J. Clin. Invest.*, vol. 99, No. 8, Apr. 1997, pp. 1991-1998.

(Continued)

*Primary Examiner*—Mark Bockelman
(74) *Attorney, Agent, or Firm*—Paul H. McDowall; Girma Wolde-Michael

(57) ABSTRACT

A medical system incorporating fluid delivery and lead delivery lumens dispense fluid into a volume of tissue. The fluid comprises or contains a pharmacologic, genetic, or biologic agent. The fluid may be dispensed initially during implantation or later using a minimally invasive medical procedure.

12 Claims, 10 Drawing Sheets

U.S. PATENT DOCUMENTS

| | | |
|---|---|---|
| 6,416,510 B1 | 7/2002 | Altman et al. ............... 606/41 |
| 6,547,787 B1 * | 4/2003 | Altman et al. ............. 604/246 |
| 6,684,109 B1 * | 1/2004 | Osypka ...................... 607/122 |
| 6,716,196 B1 * | 4/2004 | Lesh et al. ............. 604/164.01 |
| 6,726,662 B1 * | 4/2004 | Altman ....................... 604/246 |
| 6,931,286 B1 * | 8/2005 | Sigg et al. ................. 607/120 |
| 2002/0016622 A1 | 2/2002 | Janke et al. |
| 2002/0077685 A1 | 6/2002 | Sundquist et al. |
| 2003/0093104 A1 | 5/2003 | Bonner et al. |
| 2003/0191449 A1 | 10/2003 | Nash et al. ................. 604/523 |

OTHER PUBLICATIONS

Gellens et al., "Primary structure and function expression of the human cardiac tetrodotoxin-insensitive voltage-dependent sodium channel", *Proc. Natl. Acad. Sci. USA*, vol. 89, pp. 554-558, Jan. 1992.

Fozzard et al., "New Studies of the Excitatory Sodium Currents in Heart Muscle", *Circulation Research*, vol. 56, No. 4, Apr. 1985, pp. 475-485.

* cited by examiner

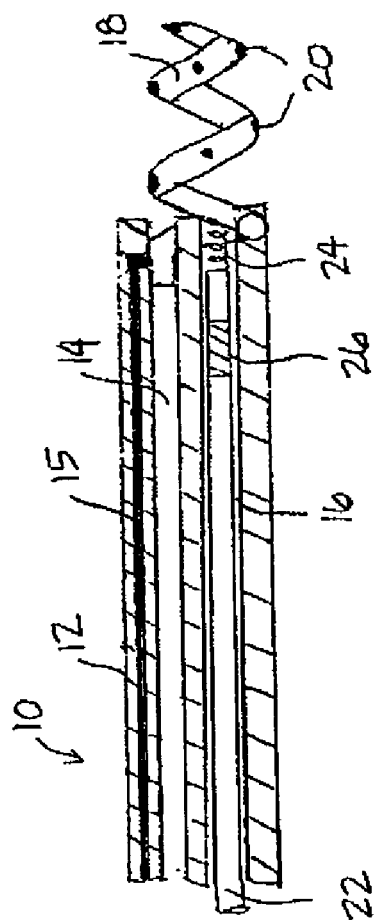
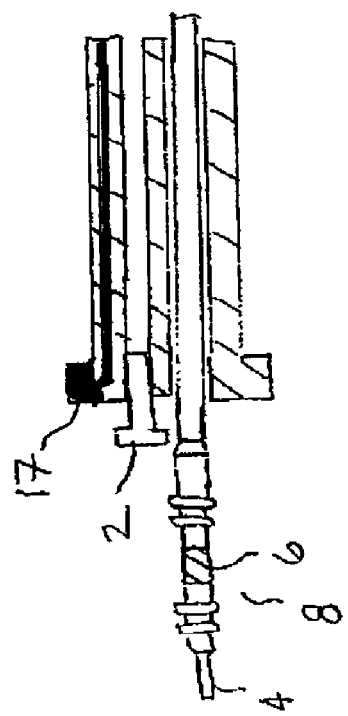
FIG. 2

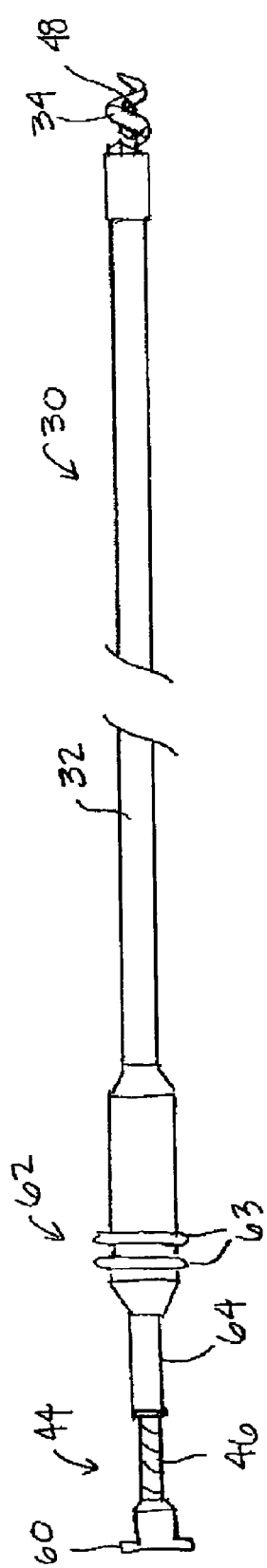
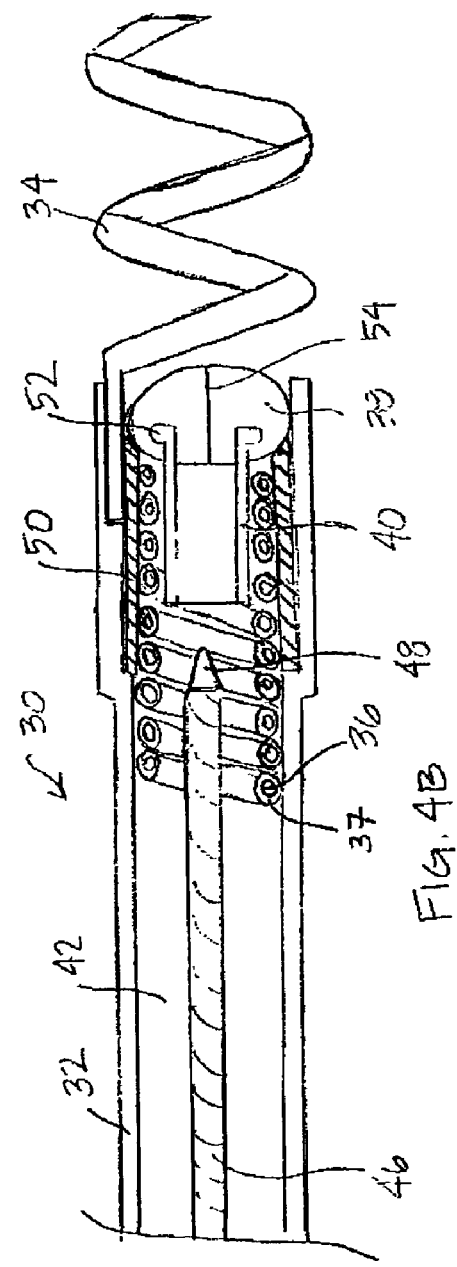
FIG. 4A
FIG. 4B

ACTIVE FLUID DELIVERY CATHETER

FIELD OF THE INVENTION

The present invention relates generally to implantable medical leads and more specifically to an implantable medical lead and fluid delivery system for treating a volume of tissue in which the medical lead may remain implanted.

BACKGROUND OF THE INVENTION

Electrical stimulation of excitable body tissue is used as a method for treating various pathological conditions. Therapeutic stimulation generally requires making an electrical contact between excitable tissue and an electrical pulse generator through use of one or more stimulation leads. Various lead systems and various techniques for implanting these lead systems in contact with excitable body tissue, and particularly the heart, have been developed.

In order to achieve cardiac pacing, sensing, cardioversion and/or defibrillation at different locations in the heart, various types of cardiac leads have been developed including epicardial leads, endocardial leads, and coronary vein leads. A transvenous endocardial lead establishes electrical contact between an electrical pulse generator, such as a pacemaker or implantable cardioverter defibrillator, and the endocardial surface of the heart, typically in a right heart chamber. Endocardial leads, and cardiac leads in general, may be held in place by passive fixation mechanisms, such as tines that interact with the ventricular trabeculae, or active fixation mechanisms, such as a helix. A coronary vein lead may be passed through a venous pathway, into the right atrium, through the coronary sinus ostium and ultimately to a location deep in the cardiac veins. Contact is made with the epicardial surface of the left atrium or left ventricle for delivering stimulation or sensing cardiac signals in the left heart chambers. Epicardial leads are also known in the art and generally require a thoracotomy for placement on the epicardial surface of a heart chamber.

The safety, efficacy and longevity of an electrical pulse generator depends, in part, on the performance of the associated cardiac lead(s) used in conjunction with the pulse generator. Various properties of the lead, the electrodes and the tissue interfacing with an electrode will result in a characteristic impedance, stimulation threshold and sensing threshold.

Stimulation threshold is the energy required in a stimulation pulse to depolarize, or "capture," the heart tissue. A relatively high impedance and low threshold is desired to minimize the current drawn from a pulse generator battery in delivering a stimulation pulse. Maximizing the useful life of the pulse generator battery is important since a surgical procedure is required to replace the pulse generator once the battery has reached the end of its useful life.

One factor that can affect the stimulation threshold, particularly during the first several weeks after implantation of a lead, is the natural immunological response of the body to the lead as a foreign object. The presence of the lead activates the immunologic response, which ultimately results in fibrotic encapsulation of the lead and its electrodes. Since fibrotic tissue is not excitable tissue, an elevated stimulation threshold can persist due to the degraded electrical properties of the electrode-tissue interface.

To reduce the inflammatory response, medical leads that elute an anti-inflammatory steroid have been developed. Steroid eluting leads are described in U.S. Pat. No. 4,506,680 issued to Stokes and related Medtronic U.S. Pat. No. 4,577,642, and 4,606,118, all incorporated herein by reference. Steroid eluting leads may require a monolithic controlled release device (MCRD) to contain the steroid and to thereafter slowly leach out the water soluble steroid into the surrounding tissue. A method for applying a steroid directly to the surface of an electrode is disclosed in U.S. Pat. No. 5,987,746 issued to Williams, incorporated herein by reference in its entirety. Advantages of this method include elimination of additional structures for carrying the steroid and the presentation of the steroid directly at the tissue-electrode interface.

One limitation of a steroid eluting electrode or MCRD, however, is that a relatively limited volume of tissue is treated by the eluting drug since the drug is presented only at the endocardial or epicardial surface. Other devices have been proposed which allow the delivery of a drug to a potentially larger volume of tissue by actually penetrating the tissue rather than relying on diffusion of the drug from the tissue surface. Drug delivery catheters may incorporate a drug dispensing needle or helix that penetrates a targeted tissue for delivering a drug or fluid. Catheters that may be used to deliver a fluid or drug into the myocardium are disclosed in U.S. Pat. No. 6,102,887 issued to Altman and U.S. Pat. No. 5,431,649 issued to Mulier et al.

Drug delivery catheters may include an electrode to allow sensing or stimulation of the myocardium. An implantable pacing lead having an active fixation electrode with a stylet introduced, anti-inflammatory drug delivery system is disclosed in U.S. Pat. No. 5,447,533 issued to Vachon et al. A delivery system for delivering a therapeutically effective amount of a genetic material to an identified cardiac location adjacent an atrial or ventricular electrode is disclosed in PCT Patent Publication WO 98/02040 issued to Stokes et al, incorporated herein by reference in its entirety. This delivery system may combine a pacing lead and a delivery catheter. Other implantable leads with drug delivery capabilities are disclosed in U.S. Pat. No. 4,360,031 to White, and U.S. Pat. No. 5,496,360 to Hoffman.

Advancements in gene therapies and cellular modifications through the delivery of proteins, peptides or even cell delivery, such as stem cell delivery, offer opportunities to alter the properties of tissue to further improve the benefit of a delivered stimulation therapy or improve the ability to sense cardiac signals. Genetic or biologic agents may be used to alter ion channel activity or protein expression at the cellular level. Potential benefits include decreased inflammatory response, increased tissue conductivity for reduction of stimulation thresholds or upregulation of ion channels for increasing membrane potentials to allow better sensing. For example, upregulation of ion channels could enhance cardiac P-waves or R-waves allowing them be more easily sensed by a pacemaker or other cardiac monitor. In particular, cardiac fast sodium channels are responsible for the fast upstroke of the action potential in myocardial cells (Fozzard, et al., Circ. Res. 1995, 56:475–485). A human cardiac voltage-dependent sodium channel, hH1, has been cloned, sequenced, and functionally expressed (Gellens, et al., Proc. Natl. Acad. Sci. USA, 1992, 89:554–558). Alteration of myocardial conductivity may be possible through delivery of proteins that alter cellular electrical coupling. The gap junction protein Connexin43 has been found to play an important role in ventricular conduction (Guerrero PA et al., J. Clin. Invest. 1997, 99:1991–1998).

Because locally effective doses of a pharmacologic, genetic, or biologic agent may be toxic when given systemically, it is desirable to provide a method for delivering an agent locally at a targeted tissue site. Drug-eluting electrodes may be limited to treating only a relatively small volume of tissue at an electrode-tissue interface. The pharmacological effect is in part limited by the kinetics of the drug leaving the electrode or lead. Furthermore, because biologic and genetic agents may have a limited shelf life, unique storage requirements such as requiring refrigeration, and may not tolerate sterilization procedures, it is not desirable to package a lead having drug eluting capabilities with the biologic or genetic agent already incorporated therein. Other medical leads having drug dispensing capabilities may require additional components that increase the size, stiffness or complexity of the lead.

To take advantage of various genetic or cellular modification therapies, it is desirable to provide an implantable lead and fluid delivery system that allows a pharmaceutical, genetic, or biologic agent to be delivered to a targeted lead implant site at a depth within the myocardium to treat a volume of tissue. Once a fluid agent has been delivered, the fluid delivery components are no longer needed and may be removed from the patient's body. An acutely implanted fluid delivery system eliminates the need to include dispensing components in the medical lead, reducing its complexity, yet still offers the benefit of treating a volume of tissue at a lead implant site, potentially improving lead performance. There is a need, therefore, for a system that allows an acutely implanted fluid delivery device to treat a volume of tissue during a lead implant procedure, or at any time post-operatively, and further allows a lead to be implanted and remain in the location of the treated tissue.

SUMMARY OF THE INVENTION

The present invention is directed toward providing a medical lead and fluid delivery system for treating a volume of tissue with a pharmaceutical, genetic, or biologic agent at the time of the medical lead implant and/or at any time post-operatively.

In one embodiment of the present invention, a guide catheter is provided with a fluid dispensing, fixation member at its distal end. The fixation member communicates with a lumen extending the length of the guide catheter body through which a fluid may be delivered. The fixation member, which may be provided as a hollow helix, is provided with one or more apertures for dispensing a drug into the surrounding tissue in which the helix is fixed. The fixation member may optionally function as an electrode in addition to being a fixation device. After treating a volume of tissue by dispensing a fluid through the fixation member, a medical lead, advanced through a lead-delivery lumen of the guide catheter, may be implanted in the treated tissue. The guide catheter may then be removed leaving the medical lead implanted at the treated tissue site.

In another embodiment, a system is provided including a guide catheter having a fixation member, a fluid delivery device, and an implantable lead. After fixing the guide catheter at a desired implant site, the fluid delivery device, advanced down a lumen of the guide catheter, may be used to treat a volume of tissue at that site. The fluid delivery device may then be removed and an implantable lead may be advanced through the guide catheter to the treated tissue site. The guide catheter may then be removed, leaving the lead implanted at the treated tissue site.

In alternative embodiments, a transvenous lead having a distal fixation member is provided with a center lumen through which a fluid delivery device may be advanced to treat a volume of tissue in which the lead is implanted. A seal is preferably provided at the distal end of the lead body to prevent fluid ingress. The distal fixation member may be provided as a passive or active fixation member. In one embodiment, a retractable active fixation member is provided. In another embodiment, the implantable lead may be provided as an epicardial lead.

The fluid delivery device may take the form of a hollow needle or stylet that may be advanced through a lumen of the lead body, penetrated through the seal and into the targeted tissue site. The fluid delivery device may be provided with a conductive tip to allow sensing of electrophysiological signals. Fluid delivery may be performed once the delivery device is inserted in the targeted tissue location as verified by sensing electrophysiological signals characteristic of the targeted tissue. After delivery of a fluid, which may be a pharmaceutical, genetic or biologic agent carried in a liquid medium, the fluid delivery device may be removed, leaving the transvenous lead implanted at the treated tissue site.

The medical lead may further include a reservoir that may be filled by the fluid delivery device with a pharmaceutical, genetic or biologic agent. The agent will elute from the reservoir into surrounding tissue over time. Treatment of a volume of tissue with a pharmaceutical, genetic or biologic agent may thus be treated by delivering a bolus injection directly into the tissue or slow elution of the agent over time, or both.

A fluid may be delivered post-operatively by gaining access to the lumen of an implanted lead through an access port on the implanted device to which the lead is connected. Multiple injections at the lead implant site at various time intervals are possible by inserting a fluid delivery device through the access port and advancing it through the lead lumen. Fluid may be delivered directly to the lead implant site, or a fluid reservoir may be refilled.

Thus, the present invention provides a medical lead and fluid delivery system that allows a lead to be implanted in a volume of tissue treated concurrently with the lead implant procedure, or at any time post-operatively, by an acutely delivered fluid delivery device.

BRIEF DESCRIPTION OF THE DRAWINGS

FIG. 2 is a side, cut-away view of an alternative embodiment of the guide catheter shown in FIG. 1 in which a fixation member on the guide catheter may also function as an electrode.

FIG. 4A is a plan view of an alternative embodiment of an implantable lead and fluid delivery system including a transvenous medical lead and a fluid delivery device that may be deployed through a lumen of the lead.

FIG. 4B is a side cut-away, view of the distal end of the system of FIG. 4A.

DETAILED DESCRIPTION OF THE INVENTION

Figure 1:
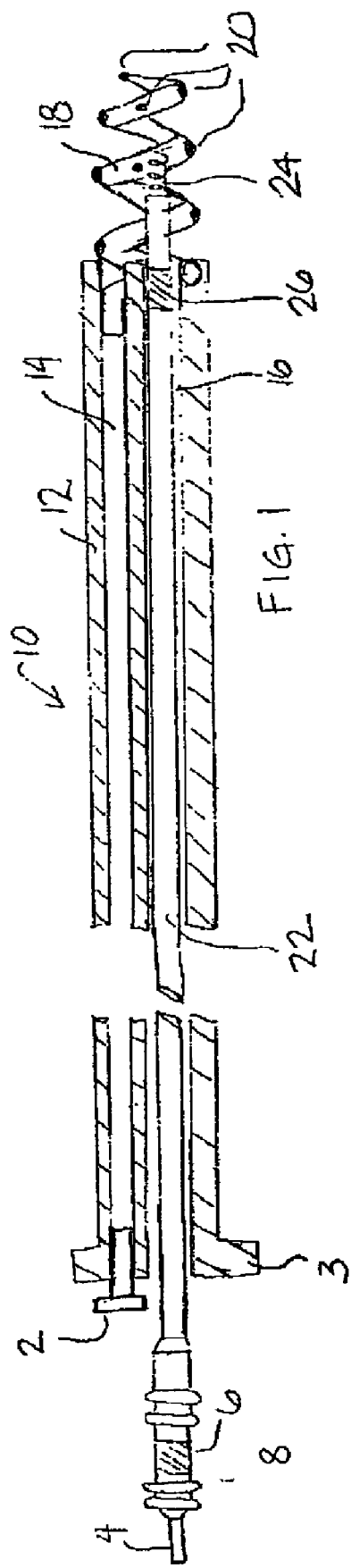
FIG. 1 is a side, cut-away view of an implantable lead and fluid delivery system including a guide catheter having fluid dispensing capabilities and an implantable medical lead.

As described above, the present invention is directed at providing an implantable lead and fluid delivery system in which a fluid delivery device may be used to treat a volume of tissue concurrently with a lead implantation procedure, or at any time post-operatively. After delivering a fluid, the fluid delivery device may be removed leaving the lead implanted at the treated tissue site. FIG. 1 is a side, cut-away view of one embodiment of an implantable lead and fluid delivery system in accordance with the present invention. The system includes a guide catheter 10 having fluid dispensing capabilities. Catheter 10 is provided with a proximal handle 3 and an elongated catheter body 12 having at least two lumens 14 and 16 and is preferably formed from a biocompatible polymer such as polyurethane, silicone, Teflon®, or other acceptable plastic. A fluid-delivery lumen 14 is in communication with an active fixation, fluid dispensing member shown as a hollow fixation helix 18 located at the distal end of guide catheter 10. An active fixation, fluid dispensing member may alternatively be provided as a hollow "fish hook" type member, stake-like member, or any other type of active fixation member that can be provided as a hollow structure having one or more apertures. Hollow fixation helix 18 is provided with one or more apertures 20 through which fluid injected through lumen 14 may exit into a tissue site. Fixation helix 18 is preferably formed from a biocompatible metal, such as stainless steel, in which apertures 20 may be formed by laser drilling. A hollow fixation helix that may be used for fluid delivery is disclosed in the '649 patent issued to Mulier et al., incorporated herein by reference in its entirety, and the WO 98/02040 patent issued to Stokes et al. A fluid fitting 2, such as a Luer lock fitting, may be inserted or mounted at the proximal end of fluid delivery lumen 14 to allow connection of a syringe for injecting fluid into lumen 14.

Catheter 10 may be provided as a steerable catheter having a manipulative handle and steering mechanism, such as a pull wire, to aid in maneuvering catheter 10 through body vessels or organs. Steering mechanisms included in catheter 10 may be embodied as generally described in U.S. Pat. No. 5,396,902, issued to Brennen, et al., for example, or U.S. Pat. No. 5,807,249 issued to Qin, et al., both patents incorporated herein by reference in their entirety.

A lead-delivery lumen 16 is provided for delivering an implantable lead 22 to a desired implant site. The lead-delivery lumen 16 is sized to allow lead 22 to easily pass through guide catheter 10 without undue friction or resistance. Lead 22 is shown as an exemplary bipolar lead having a helical tip electrode 24 located at the distal lead end and a ring electrode 26 spaced proximally from tip electrode 24. In other embodiments, lead 22 may be a unipolar, bipolar, or multipolar lead carrying any combination of tip, ring and/or coil electrodes or other sensors. Lead 22 is shown with an active fixation helical electrode 24 but could also be provided with other types of active fixation electrodes or mechanisms, such as a "fish hook" electrode. Lead 22 may alternatively be provided with a generally spherical, hemispherical or ring-shaped tip electrode with passive fixation mechanisms, such as tines as generally known in the art.

A connector assembly 8 is provided at the proximal lead end with a pin connector 4 and ring connector 6 which are electrically coupled to respective conductors that extend to tip electrode 24 and ring electrode 26. Conductors extending the length of lead 22 may be coiled conductors or cabled or stranded conductors as is known in the art.

During a lead implantation procedure, guide catheter 10 may be passed through a venous pathway into a desired heart chamber until a desired implantation site is reached. A guide wire or electrophysiological mapping catheter, passed through inner lumen 16, could be used for passage of the catheter through the venous and cardiac anatomy to allow access to the targeted tissue. This guide wire or electrophysiological catheter could be steerable and would provide the additional benefit of protecting helix 18 to prevent snagging or entanglement with anatomic structures. Fixation helix 18 is advanced into the myocardial wall by rotating catheter 10 at its proximal end. Catheter body 12 is therefore provided with torsional stiffness adequate to translate rotational force to the distal fixation helix 18. A fluid, which may be a pharmacological, genetic, or biologic agent, may then be injected into drug-delivery lumen 14 such that it is dispersed out of apertures 20 into the tissue surrounding fixation helix 18. A relatively large volume of tissue may be treated by the relatively large helix 18 on guide catheter 10.

Lead 22 may then be passed through lead delivery lumen 16 and implanted at the treated tissue site by advancing helical tip electrode 24 into the tissue. The position of guide catheter 10 is maintained by helix 18 such that lead 22 may be implanted in the same volume of tissue treated by the injection of fluid through helix 18. After implanting lead 22, guide catheter 10 may be removed by rotating catheter 10 in an appropriate direction to remove helix 18 from the tissue site and withdrawing catheter 10 over lead 22. Catheter 10 may be provided as a splittable or slittable catheter such that it may be removed from lead 22 without passing it over connector assembly 8. Alternatively, connector assembly 8 may be provided as a low profile connector assembly sized to allow catheter 10 to be readily passed over assembly 8.

FIG. 2 is a side, cut away plan view of an alternative embodiment of the guide catheter 10 shown in FIG. 1 in which the distal fluid dispensing, fixation member, helix 18, may function as an electrode. In FIG. 2, all identically labeled components correspond to those illustrated in FIG. 1. In FIG. 2, however, fixation helix 18 is shown coupled to a conductor 15 that extends the length of catheter body 12 to a proximal terminal 17 enabling connection to a monitoring device, such as an electrocardiogram monitor. Helix 18 may thus serve as an electrode allowing electrophysiological signals to be sensed and monitored in order to verify that guide catheter 10 is fixed in a desired location. Monitoring of electrophysiological signals may also aid in verifying a short-term pharmacological effect after delivering a fluid through lumen 14 and helix 18.

Figure 3A:
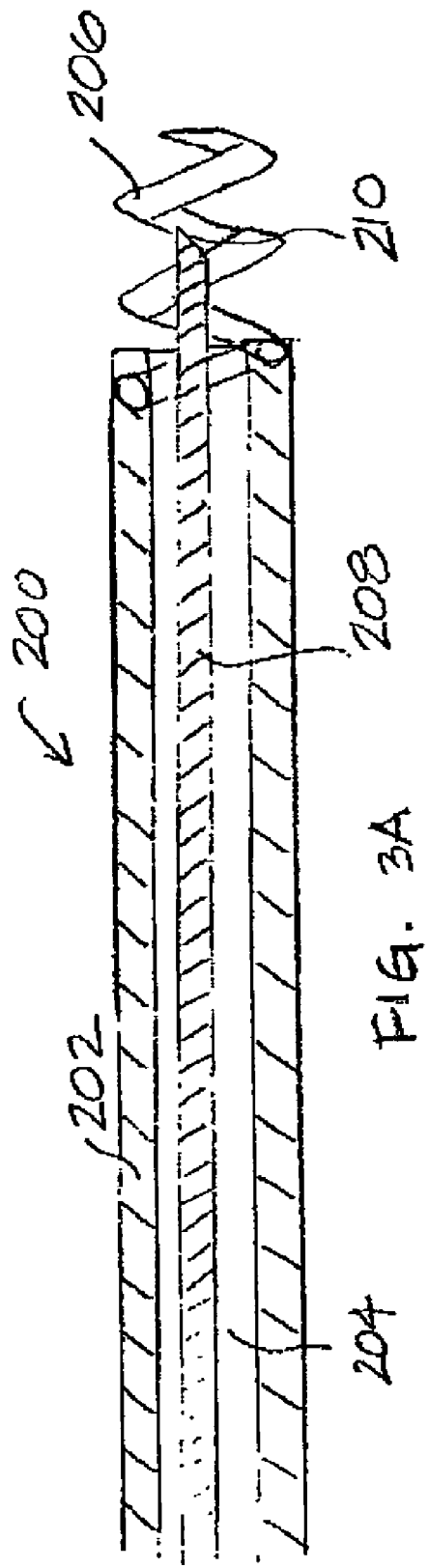
FIGS. 3A and 3B are side, cut-away views of the distal end of an implantable medical lead and fluid delivery system that includes a guide catheter, a fluid delivery device and a medical lead.
Figure 3B:
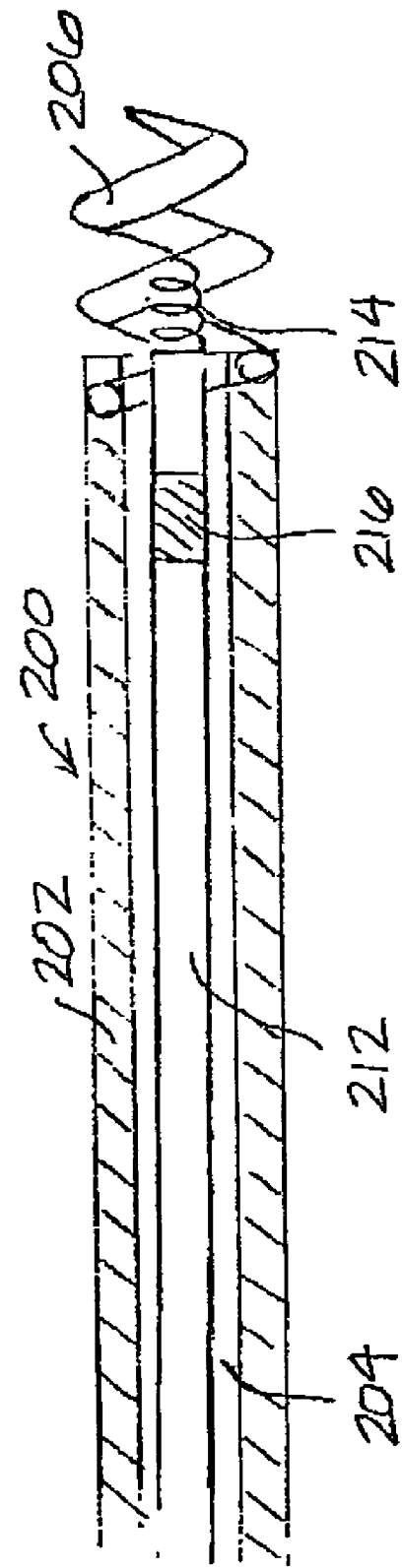

FIGS. 3A and 3B are cut-away plan views of the distal end of an implantable medical lead and fluid delivery system that includes a guide catheter 200, a fluid delivery device 208, and a medical lead 212. FIG. 3A shows a guide catheter 200 having an elongated, tubular catheter body 202 with inner lumen 204. Guide catheter 200 is provided with a fixation member 206, shown in this embodiment as a helix, that allows catheter 200 to be fixed at a targeted implant site. Fixation member 206 may be a solid helix and may function exclusively as a fixation device. Alternatively, fixation member 206 may also function as an electrode as described above with reference to FIG. 2.

A separate fluid delivery device 208 may be advanced through catheter lumen 204 until device 208 exits the distal end of catheter 200. Fluid delivery device 208, which may generally take the form of a hollow needle or stylet, may be tapered at its distal end and is preferably provided with a sharpened or beveled tip 210 such that it may easily pierce the tissue at the targeted implant site. The tip 210 may also take the form of a helix or other shape that may penetrate the tissue to a desired depth and dispense a fluid through one or more apertures to treat a volume of tissue. Once fluid delivery device 208 is advanced into the tissue, a fluid may be injected in the proximal end of fluid delivery device 208 and dispensed into a volume of tissue through tip 210.

Fluid delivery device 208 may also serve as an electrode, alternatively or in addition to helix 206 of catheter 200. Fluid delivery device 208, which may be formed from a conductive metal such as stainless steel, may be provided with an insulating coating, such as a coating of ethylene tetrafluoroethylene (ETFE) or Parylene, except for at distal tip 210. The proximal end of device 208 may be coupled to a monitor such that electrophysiological signals sensed at uninsulated tip 210 may be monitored. Verification that tip 210 is in a desired tissue site, and not in blood or non-excitable tissue, may be made by monitoring electrophysiological signals sensed at tip 210.

After dispensing a fluid into the targeted implant site, the fluid delivery device 208 may be withdrawn from lumen 204 of guide catheter 200 and replaced with an implantable medical lead 212 as shown in FIG. 3B. Lead 212 is shown as an exemplary bipolar lead having an active fixation helical tip electrode 214 at its distal end and a ring electrode 216 spaced proximally from tip electrode 214. Lead 212 may be advanced through lumen 204 and implanted at the treated tissue site by advancing helical tip electrode 214 into the tissue. Guide catheter 200 may then be removed, leaving the electrode 214 implanted in the treated tissue.

FIG. 4A is a plan view of an alternative embodiment of an implantable lead and fluid delivery system. This system includes a transvenous lead 30 and a fluid delivery device 44. The lead 30 has an elongated, tubular lead body 32. Lead body 32 may be formed from a resilient, biocompatible polymer, such as silicone or polyurethane. Lead 30 is shown as a unipolar lead having an active fixation tip electrode 34 located at its distal end, shown as a helical electrode. Lead 30 may alternatively be a bipolar or multipolar lead having, in addition to active fixation tip electrode 32, one or more ring electrodes and/or one or more coil electrodes.

A connector assembly 62 is provided at the proximal lead end to allow connection of lead 30 to an implantable pulse generator or monitoring device. Connector assembly 62 includes a pin terminal 64 that is electrically coupled to tip electrode 48 via a conductor extending the length of lead body 32. Pin terminal 64 is provided as a hollow pin that is in communication with a central lumen of lead body 32. Sealing rings 63 form a fluid-tight seal with the inner surface of a connector port on an implantable pulse generator or monitoring device.

Fluid delivery device 44 is shown inserted into the proximal end of hollow pin terminal 44. Fluid delivery device 44 may take the form of a hollow needle or stylet as described above in conjunction with FIG. 3A. Fluid delivery device 44 includes a hollow shaft 46 sized to pass easily through pin terminal 64 and the lumen of lead body 32 such that distal tip 48 of fluid delivery device 44 may exit the distal end of lead 30. A fluid fitting 60, which may take the form of a Luer lock fitting, is provided at the proximal end of device 44 to allow connection of a syringe for injecting fluid through shaft 46 to be dispensed from tip 48.

FIG. 4B is a side cut-away view of the distal end of lead 30 and fluid delivery device 44. Helical tip electrode 34 is electrically coupled to a conductive sleeve 50, preferably by laser or resistance welding. Conductive sleeve 50 is electrically coupled to a conductor 36. Conductor 36 extends to connector assembly 62 at the proximal end of lead 30 and is coupled to pin terminal 64. Conductive sleeve 50 may be coupled to conductor 36 by crimping conductive sleeve 50 such that it is compressed against conductor 36, which is supported on its internal diameter by internal sleeve 40. In this way, electrode 34 is electrically coupled to conductor 36 and pin terminal 64.

Conductor 36 is preferably a coiled conductor provided with insulation 37. Insulation 37 may be provided as a coating formed from an appropriate insulating material such as polytetrafluoroethylene (PTFE) or ETFE, preferably surrounding each individual filar included in conductor 36. Insulation 37 may alternatively be provided as heat shrink tubing fabricated from PTFE or ETFE as generally described in U.S. Pat. No. 6,052,625 issued to Marshall, incorporated herein by reference in its entirety. Conductor 36 may alternatively be provided as an insulated cabled or stranded conductor, such as the conductor generally disclosed in U.S. Pat. No. 5,246,014 issued to Williams. Insulation 37 may also be provided as a material having a high Young's modulus, such as a high durometer polyurethane or polyimide, to impart additional lead body stiffness to the small diameter lead as generally described in U.S. Pat. No. 6,366,819 issued to Stokes, incorporated herein by reference in its entirety.

Insulation 37 electrically isolates conductor 36 from tip 48 and shaft 46 of fluid dispensing device 44 allowing distal tip 48 to function as a sensing electrode for detecting electrophysiological signals at a tissue site. When tip 48 is used as a sensing electrode, fluid delivery device 44 may also be insulated along the entire length of shaft 46, particularly if conductor 36 is not provided with insulation. Distal tip 48 remains uninsulated. Insulation on shaft 46 may be provided by an adhesive coating, such as silicone adhesive, or as a tubular sleeve formed from an insulating material such as PTFE, ETFE or Parylene. A conductive clamp, connected to a monitor such as an ECG monitor, may be coupled to fitting 60 at the proximal end of fluid delivery device 44 for observing electrophysiological signals at the site in which the uninsulated tip 48 is in contact. For example, cardiac P-waves or R-waves could be sensed by tip 48.

Lead 30 is preferably provided with a seal 38 to prevent the ingress of body fluids. Seal 38 is generally cup shaped and may be formed from a resilient, biocompatible polymer, such as molded silicone rubber. Seal 38 is shown in FIG. 4B to be molded onto internal sleeve 40, which is preferably formed from a rigid, insulating material such as Delrin®, available from DuPont. Internal sleeve 40 is provided with an annular, laterally extending flange 52. Seal 38 is retained by the interaction of flange 52 and conductive sleeve 50. Seal 38 may be provided as generally described in U.S. Pat. No. 6,192,280 issued to Sommer et al., incorporated herein by reference in its entirety. Alternatively, the seal 38 can be fabricated such that it is entirely contained within a portion of conductor 36 at a point at the distal end of the lead 32 or at a location more proximal. Alternative embodiments of a seal at or near the distal end of a medical lead or medical device that may be adapted for use with the present invention are disclosed in U.S. Pat. Application 20020016622 to Janke et al., and U.S. Pat. Application 20020077685 to Sundquist et al., both of which are incorporated herein by reference in their entirety. Other types of seals for preventing fluid from entering a tubular body may also be used.

During an implantation procedure, lead 30 may be deployed to a desired implant site. Lead 30 deployment may be performed with the aid of a guide wire, stylet, or guide catheter. Helical tip electrode 34 may then be fixed in the tissue at the implant site. If a guide wire or stylet is used, it is removed from lumen 42 after lead 30 is positioned so that fluid delivery device 44 may be advanced through lumen 42. Fluid delivery device tip 48 is preferably sharpened or beveled such that it can easily pierce through seal 38. The fluid delivery device 46 might also be shapeable, allowing it to be used for positioning of the lead 32. Seal 38 may be pre-pierced at line 54 to define a path for the fluid delivery device 44 to pass through. Tip 48 is then further advanced into the implant site. Verification that tip 48 is in a desired implant site may be made by monitoring electrophysiological signals sensed by uninsulated tip 48. If no signal is sensed, tip 48 may not be advanced completely through seal 38 or may not be fully inserted into the tissue site. Once tip 48 is adequately advanced into the implant site, a fluid may be injected through device 44 to treat a volume of tissue in which helical tip electrode 34 is implanted. Fluid delivery device 44 may then be withdrawn and removed, leaving lead 30 implanted with helical tip electrode 34 fixed in the treated tissue.

Figure 5:
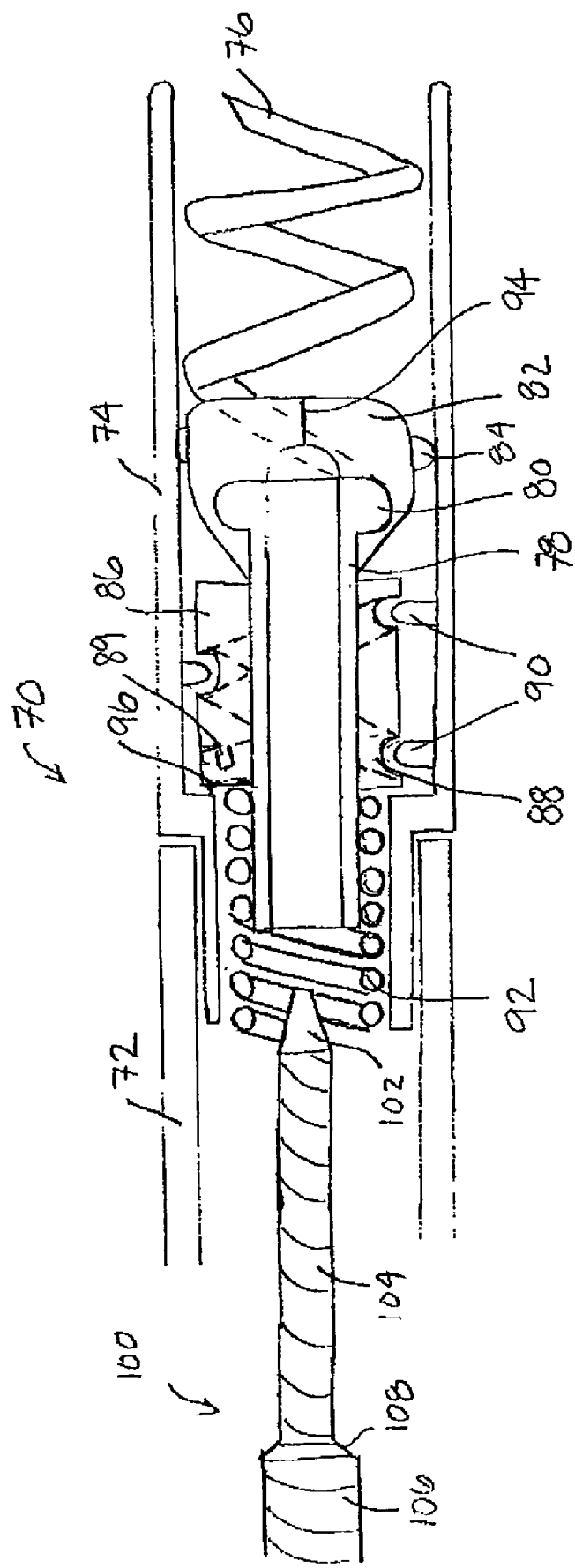
FIG. 5 is an exploded, side, cut-away view of the distal end of an implantable lead and fluid delivery system in which the lead is provided with a retractable fixation member.

FIG. 5 is an exploded, cut-away plan view of the distal end of an implantable lead and fluid delivery system wherein the lead 70 is provided with a retractable fixation member. A lead 70 is provided with a helical tip electrode 76 that may be retracted into an electrode housing 74. Electrode housing 74 is preferably formed from a relatively rigid biocompatible polymer, such as polyurethane. Housing 74 is bonded to an elongated, tubular lead body 72, which may be formed of polyurethane, silicone rubber, or another biocompatible polymer.

Helical tip electrode 76 is mounted on a conductive sleeve 78, which is electrically coupled to a conductor 92. Conductive sleeve 78, which is preferably machined from a conductive metal such as stainless steel, includes a retraction mechanism shown as a threaded barrel 86 that is coaxial with sleeve 78 and located on the outer diameter of sleeve 78. Thread 88, running along the outer surface of barrel 86, acts to engage multiple thread guides 90 mounted on the inner diameter of housing 74. Conductor 92 may be rotated relative to lead body 72 by rotating a connector pin to which conductor 92 is coupled at its proximal end. Rotation of a coiled conductor may be achieved as generally described in U.S. Pat. No. 4,106,512, issued to Bisping, incorporated herein by reference in its entirety. Rotation of conductor 92 causes rotation of sleeve 80 relative to electrode housing 74. Rotation of sleeve 80 causes advancement of helical electrode 76 as threaded barrel 86 is actuated on thread guides 90. A stop mechanism 89 may be provided as a ridge or peg near the proximal end of thread 88 that engages a thread guide 90 to prevent over extension of helical electrode 76. During retraction, threaded barrel 86 will interact with housing 74 at lateral face 96 to prevent over-retraction of helix 76. Alternatively, a stop mechanism may be provided near the distal end of thread 88 to prevent over-retraction of helix 76. A retraction stop mechanism that may be adapted for use in the present invention is disclosed in U.S. Pat. No. 5,837,006, issued to Ocel et al., incorporated herein by reference in its entirety.

Lead 70 is provided with a seal 82, preferably formed of a resilient biocompatible polymer such as silicone rubber, molded to the distal end of the conductive sleeve 78 to prevent ingress of body fluids. Seal 82 may be generally cup shaped and may be pre-pierced at line 94 to guide a fluid delivery device 100 as it passes through seal 82. Seal 82 further includes an annular sealing ring 84, coaxial with seal 82 and extending laterally from the outer diameter of seal 82. Sealing ring 84 interacts with the inner surface of housing 74 to complete a fluid-tight seal of the distal end of lead 70. Sealing ring 84 further acts to center helix 76 within housing 74.

A fluid delivery device 100 is provided which may be generally in the form of a hollow stylet or needle having an elongated shaft 106 extending between a proximal end through which fluid may be injected and a distal tip 102 through which fluid may be dispensed. Distal tip 102 is sharpened or beveled such that it may easily pierce through seal 82 and enter a targeted tissue site. A distal segment 104 of fluid delivery device 100 is provided with a reduced diameter allowing it to extend through conductive sleeve 78 such that distal tip 102 may extend out of housing 74 when helix 76 is extended into a tissue site. Lateral face 108 may act as a mechanical stop by interacting with the distal end of sleeve 78 and thereby control the maximum depth that fluid delivery device 100 is inserted into the targeted tissue site. The outer dimensions of shaft 106 and distal segment 104 and the spacing of lateral face 108 from distal tip 102 may alternatively be dimensioned to provide a stopping interface that interacts with a reduced inner diameter of sleeve 78 or helix 76. Alternatively, the tip of helix 76 may be bent to cross the center axis of helix 76 to act as a stop for fluid delivery device 100. Any of these methods for providing a mechanical stop for fluid delivery device 100 allows the tissue depth at which the fluid is injected to be controlled.

Figure 6:
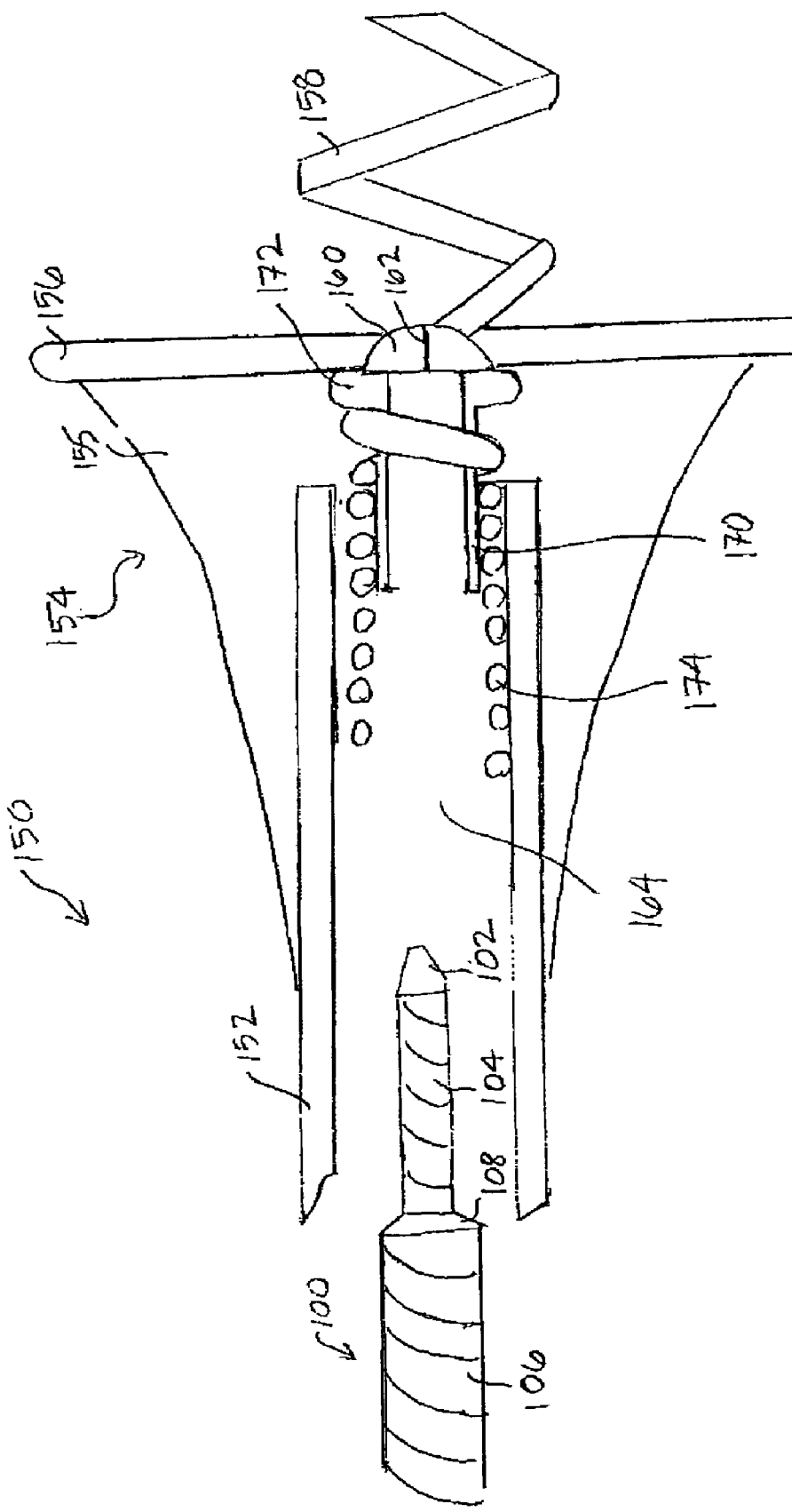
FIG. 6 is an exploded, side, cut-away view of the distal end of an implantable medical lead and fluid delivery system for use on the epicardial surface of the heart.

FIG. 6 is an exploded, cut-away side view of the distal end of an implantable medical lead and fluid delivery system for use on the epicardial surface of the heart. A lead 150 is provided with a lead body 152, an insulating electrode head 154 and an active fixation electrode 158. Electrode 158 is shown as a helical electrode but may also take the form of a "fish hook" type electrode, or any other active fixation electrode. Electrode head 154 includes a tapered body 155 and flange 156, both of which may be formed from silicone rubber and provide a flexible structure for stabilizing the position of lead 150 on the epicardial surface. A tool may be used for implanting lead 150 by attaching to and rotating the electrode head 154 to screw the helical electrode 158 into the epicardium as is generally known in the art. Epicardial leads and tools for implanting epicardial leads are disclosed in U.S. Pat. No. 3,737,539 issued to Bolduc, U.S. Pat. No. 5,143,090 issued to Dutcher, and U.S. Pat. No. 6,010,526 issued to Sandstrom et al., all of which patents are incorporated herein by reference in their entirety. Flange 156 may be reinforced with an embedded netting or mesh material, such as polyester netting. Netting material may optionally be coated with an anti-inflammatory steroid to reduce the inflammatory response at the tissue-lead interface.

Helical electrode 158 is electrically coupled to a conductive sleeve 170, which is further coupled to a conductor 174, shown as a coiled conductor. Conductive sleeve 170 is provided with an annular flange 172. A seal 160 is molded to flange 172 to prevent the ingress of bodily fluids into the lead body lumen 164. Seal 160 may be pre-pierced at line 162 to define a path for fluid delivery device 100 to pass through. Fluid delivery device 100 may correspond to the fluid delivery device shown in FIG. 5 and is shown in FIG. 6 with identically labeled components corresponding to those in FIG. 5. Lateral face 108 may engage with the proximal end of conductive sleeve to control the depth that fluid delivery device 100 is inserted into the tissue.

After implanting lead 150, fluid delivery device 100 may be extended through lead body lumen 164 and seal 160 to dispense a fluid into the tissue surrounding helical electrode 158. Fluid delivery device 100 may then be withdrawn from lumen 164 and removed from the patient's body, leaving lead 150 implanted at the treated tissue site.

Figure 7:
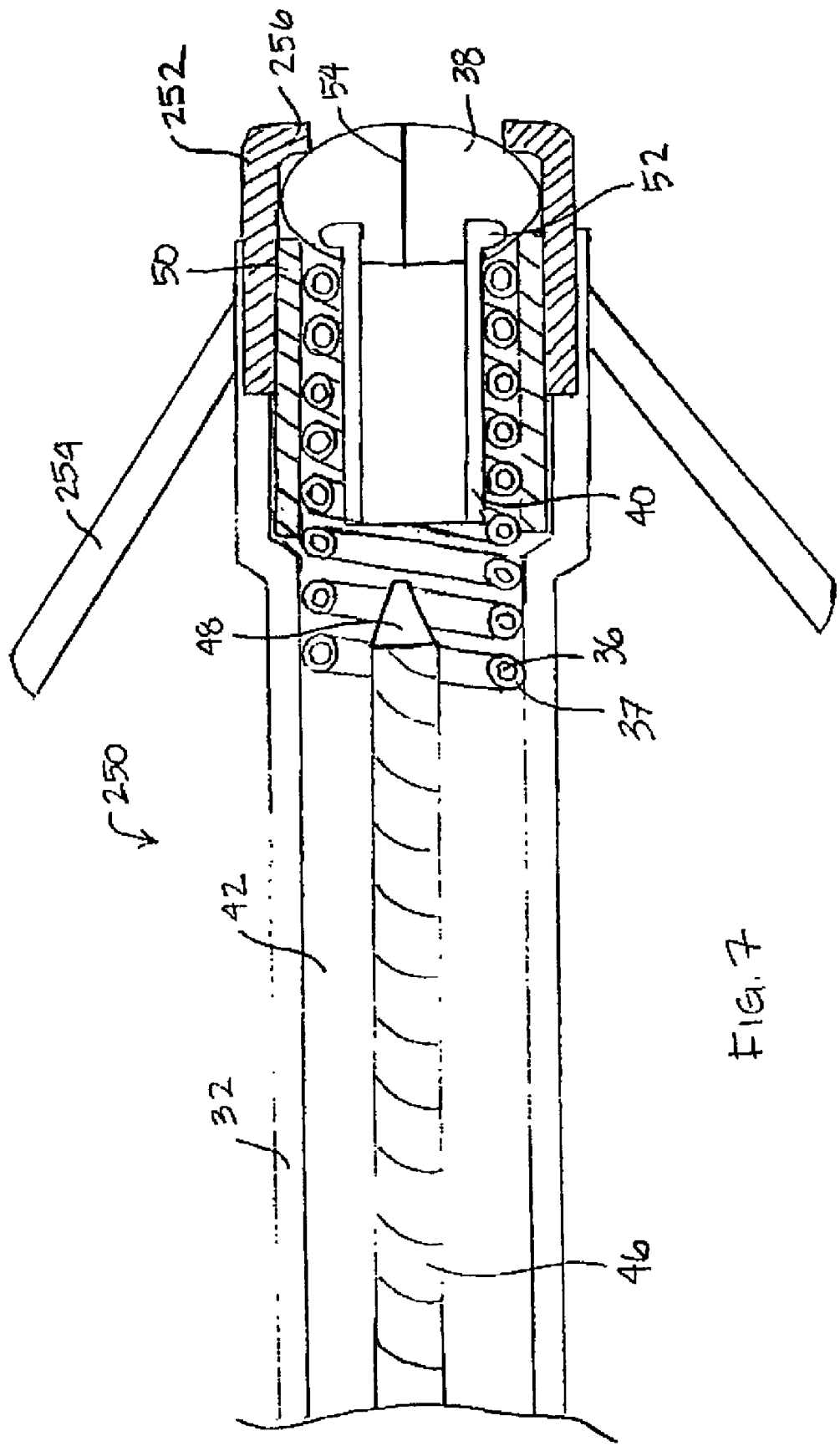
FIG. 7 is a cut-away, side view of the distal end of an implantable medical lead and fluid delivery system wherein the medical lead is provided as a transvenous lead having a passive fixation mechanism.

FIG. 7 is a cut-away, side view of the distal end of an implantable medical lead and fluid delivery system wherein the medical lead is provided as a transvenous lead having a passive fixation mechanism. In this embodiment, all identically labeled components correspond to those illustrated in FIG. 4B, however, in this case, in place of an active fixation electrode at the tip of the lead 250, a ring electrode 252 is provided. Ring electrode 252 is electrically coupled to conductive sleeve 50, which is further coupled to insulated conductor 36 as previously described with reference to FIG. 4B. To stabilize the implanted position of lead 252, passive fixation members 254 are provided, which may take the form of tines as is generally known in the art. Seal 38 may be molded onto internal sleeve 40 as described previously and forms a fluid-tight seal with the inner diameter of ring electrode 252. Ring electrode 252 may be provided with an annular lip 256 which may act to retain seal 38.

Figure 8:
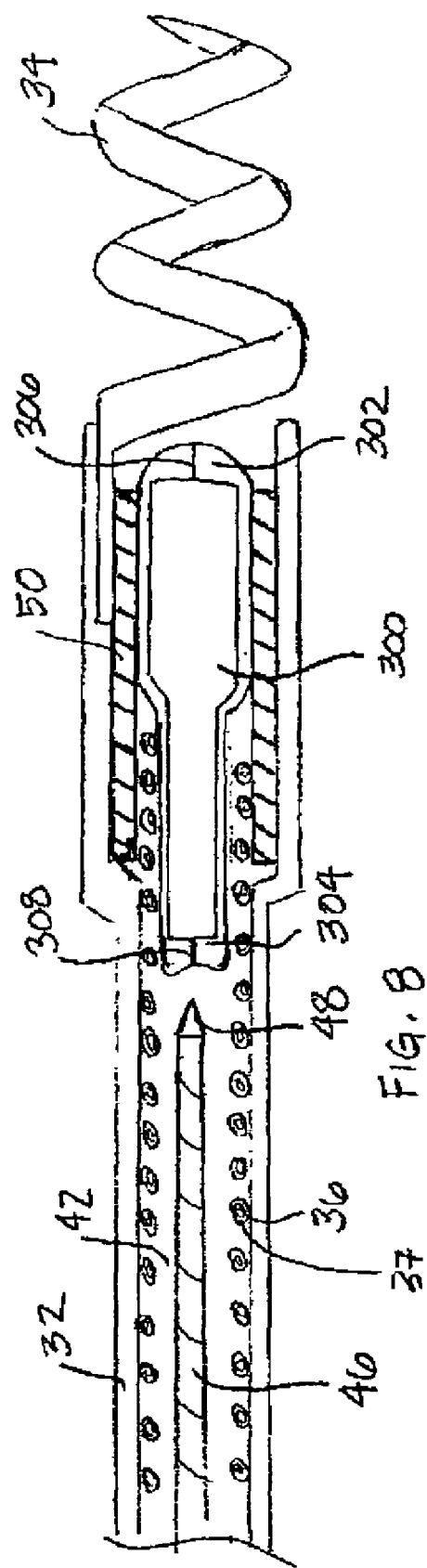
FIG. 8 is side, cut-away view of the distal end of an implantable medical lead and fluid delivery system wherein the medical lead is further provided with a fluid reservoir for holding a pharmaceutical, genetic or biologic agent and allowing the agent to elute into adjacent body tissue over time.
Figure 9:
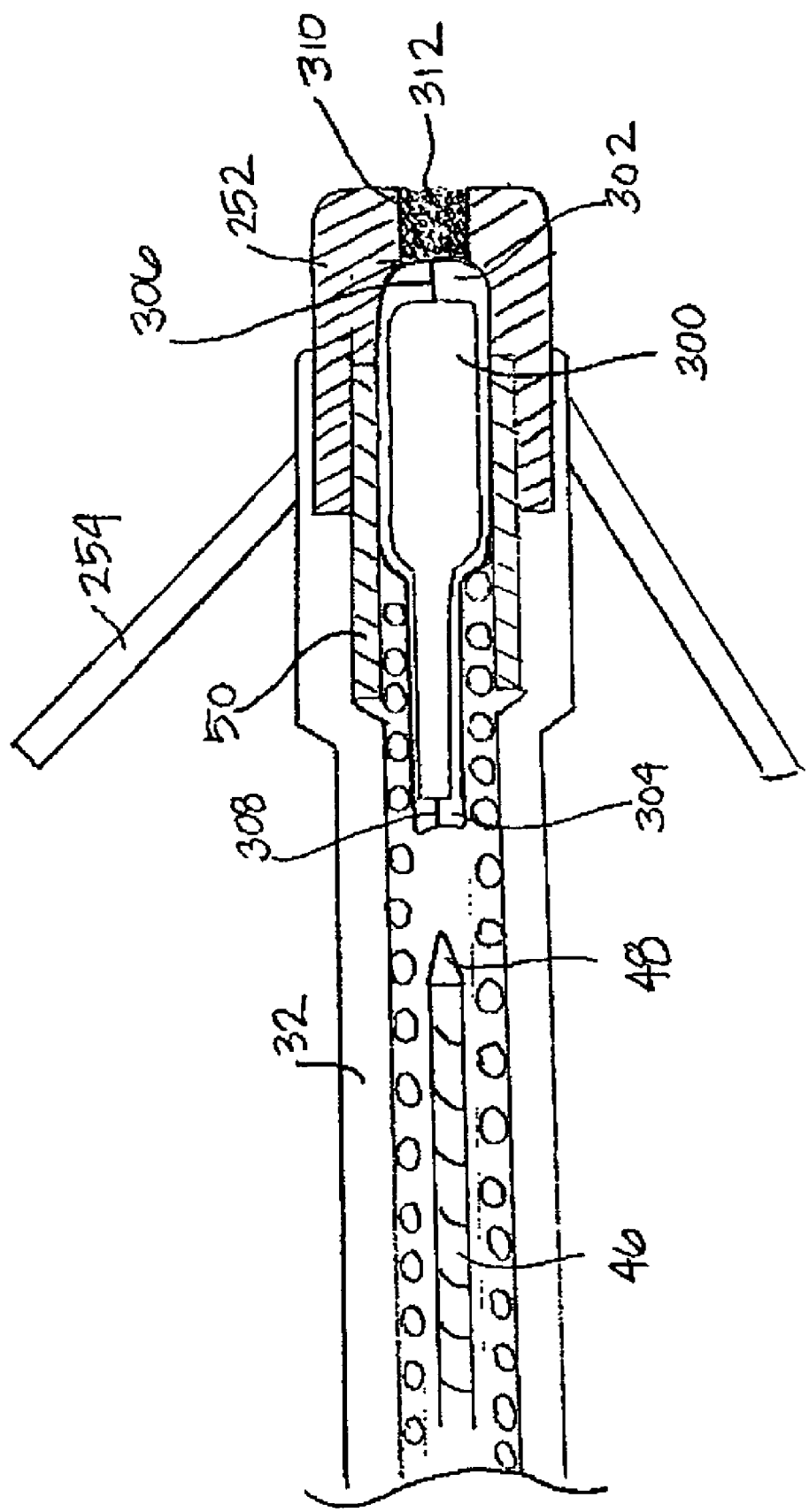
FIG. 9 is a side, cut-away view of the distal end of an implantable medical lead and fluid delivery system wherein the medical lead is provided as a transvenous lead having a passive fixation mechanism and a fluid reservoir.

FIGS. 8 and 9 are side, cut-away views of the distal end of an implantable medical lead and fluid delivery system wherein the medical lead is further provided with a fluid reservoir for holding a pharmaceutical, genetic or biologic agent and allowing the agent to elute into adjacent body tissue over time. A body implantable lead having a cavity suitable for retaining a drug is disclosed in U.S. Pat. No. 4,506,680 issued to Stokes, incorporated herein by reference in its entirety. A combined catheter and reservoir, useful for applications involving delivery of genetic material, is disclosed in the previously cited PCT Patent Publication WO 98/02040.

The lead shown in FIG. 8 corresponds to the lead of FIG. 4B having a helical tip electrode 34 electrically coupled to stem 50 which is further coupled to an insulated conductor 36. In addition to or in place of a seal at or near the distal end of the lead, a fluid reservoir 300 is located near the distal end of the lead. A fluid delivery device in the form of a hollow stylet or needle, having a shaft 46 and sharpened tip 48, may be used to fill reservoir 300 with a fluid. Reservoir 300 preferably includes a seal 304 covering a proximal opening to reservoir 300 and a seal 302 covering a distal opening to reservoir 300. Fluid delivery device tip 48 pierces through the proximal seal 304, which may be pre-pierced at line 308 and may be provided with a concave proximal surface to guide tip 48 to reservoir 300 and through seal 302. Fluid may then be injected into reservoir 300, and the fluid delivery device may be removed. The pharmaceutical, genetic, or biologic agent will elute from reservoir 300, through distal seal 302, into the adjacent tissue over time.

Fluid reservoir 300 may be formed from silicone rubber or alternatively polyurethane or another elastomer. The seals 302 and 304 are preferably formed from silicone rubber. Seal 304 may be provided as a less permeable material than seal 302 to prevent blood or bodily fluids from entering the lead body lumen 42 while still allowing a pharmaceutical, genetic or biologic material to elute through seal 304. The reservoir 300 may be provided as a micro-osmotic pump. For example reservoir 300 may optionally contain a salt-loaded silicone material, which would swell over time as salt is replaced by water, or another polymeric material capable of swelling upon exposure to body fluids. Such swelling would aid in "pumping" a fluid agent out of reservoir 300.

Optionally, the fluid delivery device may be further advanced through distal seal 302, which may be pre-pierced at line 306. The fluid delivery device may then be inserted into the tissue in which electrode 34 is implanted to deliver a bolus of fluid directly to the tissue site, at a desired depth within the tissue. The fluid delivery device may then be withdrawn into reservoir 300 and used to fill reservoir 300 to allow a pharmaceutical, genetic or biologic agent to elute slowly over time into the adjacent tissue. In this way, local treatment of a volume of tissue may be performed by delivering a bolus of fluid directly into the tissue, or allowing the agent to elute from reservoir 300 over time, or both. Furthermore, one or more fluid agents may be delivered directly into the tissue site, and another fluid agent may be used to fill reservoir 300 and elute over time allowing the volume of tissue in which electrode 34 is implanted to be treated by at least two different pharmaceutical, genetic or biologic agents over different time courses.

A fluid reservoir for storing a fluid agent that will elute over time may also be included in other embodiments of medical lead and fluid delivery systems. FIG. 9 is a cut-away, side view of the distal end of an implantable medical lead and fluid delivery system wherein the medical lead is provided as a transvenous lead having a passive fixation mechanism and a fluid reservoir. The system shown in FIG. 9 is similar to the system shown in FIG. 7, and identically labeled components correspond to those shown in FIG. 7. However, in FIG. 9, the transvenous lead is shown having a fluid reservoir 300, similar to the reservoir described above in conjunction with FIG. 8. Ring tip electrode 252 is provided with a central bore 310 that may be filled with a porous material through which a pharmaceutical, genetic or biologic agent eluting out of reservoir 300 may pass to reach adjacent body tissue. A porous elution path may be formed from sintered metal structures as disclosed in the above incorporated '680 patent. Alternatively central bore 310 may be left open, as shown previously in FIG. 7, to allow a fluid delivery device to be passed through tip electrode 252 to inject fluid directly into the tissue as well as providing an open elution pathway.

In some cases, it may be desirable to deliver a therapeutic fluid at a time after the lead implantation procedure. For example, pharmacological, genetic or biological treatments may need to be repeated at certain intervals over time post-operatively in order to achieve a desired therapeutic effect. A situation may also arise requiring a chronically implanted lead to be repositioned due to dislodgment or declining stimulation or sensing performance. It may be desirable to treat the tissue at the new implant site at the time the lead is repositioned. On the other hand, factors that may be causing poor lead function, such as poor tissue conductivity or low membrane potential signals, may be improved by treating the tissue at the chronic lead implant site with a fluid agent, thereby avoiding the need for lead repositioning.

Figure 10:
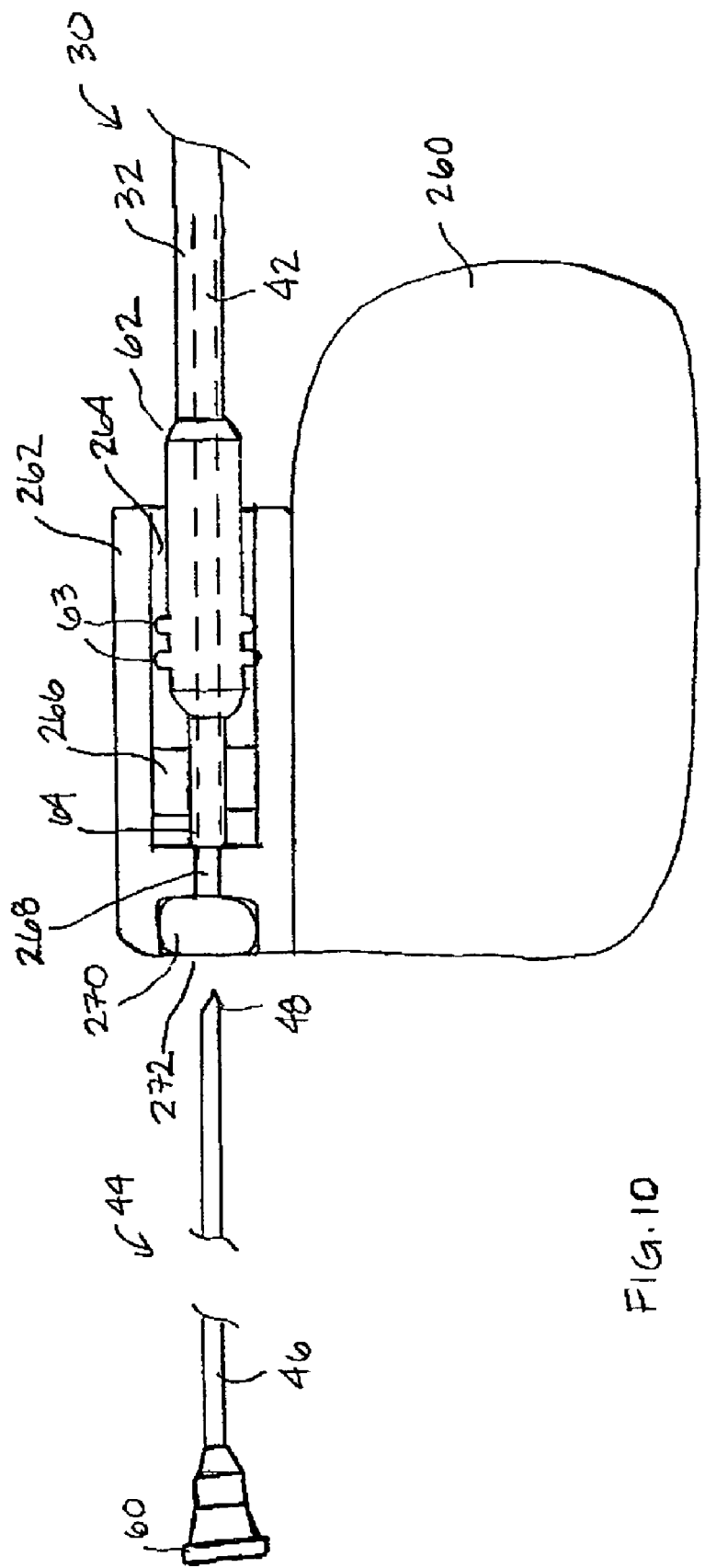
FIG. 10 is a plan view of an implantable lead and fluid delivery system that may be used to deliver a fluid agent to a lead implant site post-operatively.

FIG. 10 is a plan view of an implantable lead and fluid delivery system that may be used to deliver a fluid agent to a lead implant site post-operatively. In this embodiment, lead 30 corresponds generally to that shown in FIG. 4A, and all identically labeled components correspond to those illustrated in FIG. 4A. In FIG. 10, connector assembly 62 at the proximal end of lead 30 is inserted into a connector bore 264 of a connector block 262 provided on a medical device 260, which may be a pacemaker or implantable cardioverter defibrillator, or other type of implantable pulse generator or electrophysiological monitor. Pin terminal 64 is electrically coupled to terminal 266 of connector block 262 to provide electrical connection between lead 30 and device 260. The lumen 42 (indicated by dashed line) of lead body 32 that is continuous with hollow pin 64 communicates with a lumen 268 within connector block 262. Lumen 218 may be accessed through access port 272, which is preferably sealed against body fluids by a grommet 270. Fluid delivery device 44, which may generally correspond to the fluid delivery device described in conjunction with FIG. 4A, may be inserted through access port 272 and grommet 270 such that it may be passed through lumen 268, hollow pin terminal 64 and lead body lumen 42. Fluid delivery device 44 may then exit the distal end of lead 30 until it penetrates the tissue at the lead 30 implant site, as described previously. Once penetrated to a desired depth, fluid may be delivered through fluid delivery device 44. Fluid delivery device 44 may then be removed. Additionally or alternatively, fluid delivery device 44 may be used to refill a fluid reservoir that may be provided near the distal lead end as described in conjunction with FIGS. 8 and 9.

Access port 272 may be exposed during a minor surgical procedure by making a small skin incision at the site that device 260 is implanted. In this way, a volume of tissue at the lead implant site may advantageously be treated using a fluid delivery device at any time post-operatively without performing major surgery or catheterization procedures.

Thus, the present invention provides a system for treating a volume of tissue concurrently with a lead implant procedure such that the lead may remain implanted at the treated tissue site. The present invention further allows tissue at a lead implant site to be treated at any time post-operatively through minimally invasive procedures. The various embodiments described herein include a medical lead and fluid delivery system that allow the fluid delivery components to be removed from the patient's body after treating a targeted tissue site so that only the lead remains implanted. However, the inventive system may also be used in procedures for treating a volume of tissue in which chronic implantation of a lead is not required. The lead may be used acutely with an associated fluid delivery device to deliver a fluid agent to a targeted tissue site and then removed with the fluid delivery device rather than remaining implanted or implanted at another site. For example, other therapy modalities that may benefit from the inventive system and may or may not require chronic implantation of a lead may include treatment of myocardial infarction via cell delivery or treatment of coronary artery disease via drugs or biologic agents such as angiogenic factors. While the embodiments described herein have been described with regard to cardiac leads and the treatment of cardiac tissue, aspects of the inventive system may also be used in regard to other types of leads and other types of bodily tissue, such as kidney, brain, pancreas, or other organs or tissues. The described embodiments are therefore exemplary and should not be considered limiting with regard to the following claims.

The invention is claimed is:

1. An implantable fluid delivery system comprising: an elongate guide catheter having at least one elongated fluid delivery lumen and at least one medical electrode lead lumen disposed therein;
   a hollow, perforated fixation member in fluid communication with said at least one fluid delivery lumen, said fixation member having one of a helical coil or a fish hook configuration;
   at least one medical electrode lead member having a distal end said lead removably disposed in said at least one medical electrode lead lumen whereby the guide catheter may be removed from the body leaving the medical electrode therein, said medical electrode lead having a fixation member adjacent said distal end and being extendable from said medical electrode lead lumen, said fixation member having one of a helical coil or a fish hook configuration.

2. A system according to claim 1, wherein said medical electrical lead further comprises an electrical conductor disposed within a lead body portion and said electrical conductor is electrically coupled to said electrode structure adapted to contact tissue and said electrical conductor electrically couples to a one of the following: an implantable pulse generator, a positive pressure drug pump, a negative pressure drug pump, a micro-osmotic pump, a positive displacement pump, a solenoid-activated pump, a neurostimulator, a pacemaker, an ICD.

3. A system according to claim 2, wherein said tissue is at least a portion of one of the following types of tissue: a cardiac tissue, a nerve tissue, a muscle tissue, an organ tissue, a central nervous system tissue, a brain tissue.

4. A system according to claim 1, wherein a proximal end of said guide-catheter is sealed and adapted to be disposed proximate a portion of epidermis of a patient.

5. A system according to claim 1, wherein said guide-catheter further comprises a steerable catheter and said steerable catheter comprises a manually adjustable handle means mechanically coupled to a proximal end of the guide-catheter for providing torque to the proximal portion of said guide-catheter.

6. A system according to claim 5, wherein said handle means mechanically couples to a proximal portion of at least one pull wire and wherein said at least one pull wire is mechanically coupled to a distal portion of said guide-catheter.

7. A system according to claim 6, further comprising a fluid reservoir fluidly coupled to a delivery port of said handle means and wherein said delivery port is in fluid communication with said at least one fluid delivery lumen.

8. A system according to claim 7, wherein a fluid is pre-filled into said fluid reservoir, said fluid comprising a pharmacological agent, a genetic agent, or a biological agent.

9. A method for guiding an irrigated active fixation means to a portion of tissue, piercing said portion of tissue and dispensing a fluid therein, comprising:
   advancing a guide-catheter to a portion of tissue, wherein said guide catheter has at least one fluid delivery lumen disposed therein;
   piercing said portion of tissue with an irrigated tip portion of said guide-catheter, wherein said guide-catheter is fluidly coupled to the at least one fluid delivery lumen;

dispensing a fluid into said pierced portion of tissue through said fluid delivery lumen and said irrigated tip portion, said fluid is a pharmacological agent, a genetic agent, or a biological agent;

retracting said irrigated tip portion into a distal portion of said guide catheter;

delivering a medical electrical lead through at least one lead-delivery lumen of said guide-catheter to a location adjacent said portion of tissue; and removing said guide catheter so that said medical electrical lead remains in the location adjacent said portion of tissue.

10. A method according to claim 9, further comprising: reversing said irrigated tip portion from an original insertion depth and again dispensing the fluid.

11. A method according to claim 9, wherein said dispensing is a single shot bolus delivery.

12. A method comprising:

advancing a guide-catheter to a portion of tissue, wherein said guide catheter has at least one fluid delivery lumen disposed therein;

piercing said portion of tissue with an irrigated tip portion of said guide-catheter, wherein said guide-catheter is fluidly coupled to the at least one fluid delivery lumen;

dispensing a fluid into said pierced portion of tissue through said fluid delivery lumen and said irrigated tip portion; and delivering a medical electrical lead with an active fixation electrode tip through at least one lead-delivery lumen of said guide-catheter to a location adjacent said portion of tissue, and implanting said active fixation electrode tip in said tissue, removing said guide catheter from the body leaving the electrical lead implanted in said tissue.

* * * * *